United States Patent [19]

Schwindeman et al.

[11] Patent Number: 5,567,774

[45] Date of Patent: * Oct. 22, 1996

[54] ANIONIC POLYMERIZATION PROCESS USING FUNCTIONALIZED INITIATORS

[75] Inventors: James A. Schwindeman, Lincolnton; Eric J. Granger, Charlotte; John F. Engel, Belmont; Conrad W. Kamienski, Gastonia, all of N.C.

[73] Assignee: FMC Corporation, Philadelphia, Pa.

[*] Notice: The portion of the term of this patent subsequent to May 8, 2015, has been disclaimed.

[21] Appl. No.: 460,300

[22] Filed: Jun. 2, 1995

Related U.S. Application Data

[60] Division of Ser. No. 436,784, May 8, 1995, which is a continuation-in-part of Ser. No. 332,217, Oct. 31, 1994, abandoned, which is a continuation-in-part of Ser. No. 198,914, Feb. 18, 1994, abandoned.

[51] Int. Cl.$^6$ .............................. C08F 8/30; C08F 8/08; C08F 36/04; C08F 4/08
[52] U.S. Cl. .................. 525/272; 525/123; 525/126; 525/177; 525/184; 525/288; 525/296; 525/298; 525/303; 525/309; 525/315; 525/316; 525/332.3; 525/333.6; 525/342; 525/354; 525/366; 525/370; 525/375; 525/384; 525/385; 525/386; 526/181
[58] Field of Search .................. 526/173, 181; 525/272, 315, 316, 123, 126, 177, 184, 288, 296, 298, 384, 385, 386, 366, 303, 309, 332.3, 332.6, 342, 354, 370, 375

[56] References Cited

U.S. PATENT DOCUMENTS 3,326,881 6/1967 Uraneck et al. .................. 526/181 X
3,776,964 12/1973 Morrison et al. .................. 526/173 X
3,842,146 10/1994 Milkovich et al. .................. 526/271
3,862,100 1/1975 Halasa et al. .................. 526/181
3,954,894 5/1976 Kamienski et al. .................. 526/173 X
4,039,593 8/1977 Kamienski et al. .................. 526/173 X
5,331,058 7/1994 Shepherd et al. .................. 526/173 X
5,391,663 2/1995 Bening et al. .................. 526/178
5,416,168 5/1995 Willis et al. .................. 525/333.2

FOREIGN PATENT DOCUMENTS 2255567 6/1991 United Kingdom .

*Primary Examiner*—Fred Teskin
*Attorney, Agent, or Firm*—Charles C. Fellows; Robert L. Andersen

[57] ABSTRACT

A process for the preparation of hydrocarbon solutions of monofunctional ether initiators of the following general structure:

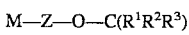

$$M-Z-O-C(R^1R^2R^3)$$

wherein M is an alkali metal; Z is a branched or straight chain hydrocarbon group which contains 3–25 carbon atoms, optionally containing aryl or substituted aryl groups; and $R^1$, $R^2$, and $R^3$ are independently selected from hydrogen, alkyl, substituted alkyl, aryl or substituted aryl groups, and their employment as initiators in the anionic polymerization of olefin containing monomers in an inert, hydrocarbon solvent comprising reacting an omega-protected-1-haloalkyl with lithium metal dispersion having a particle size between 10 and 300 millimicrons in size, at a temperature between 35° and 130° C. in an alkane solvent containing 5 to 10 carbon atoms.

16 Claims, No Drawings

ANIONIC POLYMERIZATION PROCESS USING FUNCTIONALIZED INITIATORS

This application is a divisional of application Ser. No. 08/436,784 filed May 8, 1995, which is a continuation-in-part of application Ser. No. 08/332,217 filed Oct. 31, 1994, now abandoned, which application was a continuation in part of U.S. Ser. No. 08/198,914, filed Feb. 18, 1994, also abandoned.

This invention concerns novel anionic initiators for use in polymerizing olefinic-containing monomers, a process for making the anionic initiators, a process for the polymerization of olefinic-containing monomers using the lo anionic initiators of this invention and polymers produced by this polymerization process.

Useful polymeric products are obtained by polymerizing olefinic-containing monomers in the presence of an organoalkali metal initiator and subsequently reacting the resulting polymer, containing an active alkali metal end group or groups, with a reagent which will couple the polymer molecules or replace the alkali metal with more stable reactive end groups. Monofunctional silyl ether initiators, containing alkali metal end groups useful in effecting such polymerization reactions are disclosed in Great Britain published patent application 2,241,239, published Aug. 28, 1991. These monofunctional silyl ether initiators were demonstrated to be useful in producing polydienes having desirable characteristics such as a molecular weight of typically 1,000 to 10,000, 1–4 content of typically 90%, etc.

Although analogous lithiohydrocarbyl ether compounds have been prepared and utilized in organic syntheses by M. Gardette et al, Tetrahedron, 41, 5887 [1985], these were prepared in ethereal solvents only, wherein their stability was poor and their utility as polymer initiators disadvantageous because of high solvent polarity.

The present invention provides a process for the preparation of novel, hydrocarbon solutions of monofunctional ether initiators of the following general structure:

$$M-Z-O-C(R^1R^2R^3) \quad [I]$$

wherein M is defined as an alkali metal, preferably lithium; Z is defined as a branched or straight chain hydrocarbon connecting group group which contains 3–25 carbon atoms, optionally containing aryl or substituted aryl groups; and $R^1 R^2$ and $R^3$ are independently defined as H, alkyl, substituted alkyl, aryl or substituted aryl, and their employment as initiators in the anionic polymerization of olefin containing monomers in an inert, hydrocarbon solvent, optionally containing a Lewis Base. The process reacts selected protected omega-protected-1-haloalkyls whose alkyl groups contain 3 to 25 carbon atoms, which are reacted with lithium metal in a liquid alkane, cycloalkane or aryl solvent, at a temperature between about 35° C. and about 130° C.

The initiator precursor omega-protected 1-haloalkyls (halides) are prepared from the corresponding haloalcohol by the standard literature methods. For example, 3-(1,1-dimethylethoxy)-1-chloropropane is synthesized by the reaction of 3-chloro-1-propanol with 2-methylpropene according to the method of A. Alexakis, M. Gardette, and S. Colin, Tetrahedron Letters, 29, 1988, 2951. The method of B. Figadere, X. Franck and A. Cave, Tetrahedron Letters, 34, 1993, 5893, which involved the reaction of the appropriate alcohol with 2-methyl-2-butene catalyzed by boron trifluoride etherate is employed for the preparation of the t-amyl ethers. The triphenylmethyl protected compounds, for example 3-(triphenylmethoxy)-1-chloropropane, are prepared by the reaction of the haloalcohol with triphenylmethylchloride, according to the method of S. K. Chaudhary and O. Hernandez, Tetrahedron Letters, 1979, 95. The compound 4-(methoxy)-1-chlorobutane, and the higher analogues, are synthesized by the ring opening reaction of tetrahydrofuran with thionyl chloride and methanol, according to the procedure of T. Ferrari and P. Vogel, SYNLETT, 1991, 233.

Monofunctional ether initiators (I) are prepared in accord with the process of this invention and such compounds can include, but are not limited to, 3-(1,1-dimethylethoxy)-1-propyllithium, 5-(1,1-dimethylethoxy)-1-pentyllithium, 3-(1,1-dimethylethoxy)-2,2-dimethyl-1-propyllithium, 4-(1,1 -dimethylethoxy)-1-butyllithium, 6-(1,1-dimethylethoxy)-1-hexyllithium, 8-(1,1 -dimethylethoxy)-1-octyllithium, 4-(ethoxy)-1-butyllithium, 4-(1-propyloxy)-1-butyllithium, 4-(1-methylethoxy)-1-butyllithium, 3-(triphenylmethoxy)-2,2 -dimethyl-1-propyllithium, 4-(triphenylmethoxy)-1-butyllithium, 5 -(triphenylmethoxy)-1-pentyllithium, 6-(triphenylmethoxy)-1-hexyllithium, 8-(triphenylmethoxy)-1-octyllithium, 3-(1,1-dimethylpropyloxy)-1-propyllithium, 3 -(1,1-dimethylpropyloxy)-2,2-dimethyl-1-propyllithium, 4-(1,1 -dimethylpropyloxy)-1-butyllithium, 6-(1,1-dimethylpropyloxy)-1-hexyllithium, 4 -methoxy-1-butyllithium, 3-methoxy-1-butyllithium, 3-(triphenylmethoxy)-1 -propyllithium, 3-(1,1-dimethylethoxy)-2-methyl-1-propyllithium, and 3-(1,1 -dimethylpropyloxy)-2-methyl-1-propyllithium.

Lithium metal used in preparing the monofunctional ether initiators (I) is used as a dispersion whose particle size usually does not exceed about 300 microns. Preferably the particle size is between 10 and 300 microns although coarser particle size lithium can be used. The lithium metal can contain 0.2 to 0.8 and preferably 0.3 to 0.5 weight percent sodium. The lithium metal is used in amounts of 90% of theoretical to a 40% excess above the theoretical amount necessary to produce the monofunctional ether initiators (I). The preferred reaction temperatures vary from compound to compound, with each compound tending to have its own preferred reaction conditions. Suprisingly, for some compounds the preferred reacton temperature/condition is the reflux temperature of the solvent. When this is the case the preferred reaction temperature is in the range of 35° to 80° C.

Solvents useful in practicing this invention include but are not limited to inert liquid alkanes, cycloalkanes and aryl solvents such as alkanes and cycloalkanes containing five to 10 carbon atoms such as pentane, hexane cyclohexane, methylcyclohexane, heptane, methylcycloheptane, octane, decane and so forth and aryl solvents containing six to ten carbon atoms such as toluene, ethylbenzene, p-xylene, m-xylene, o-xylene, n-propylbenzene, isopropylbenzene, n-butylbenzene, and the like.

Advantages of using the compounds containing the protecting groups of this invention comprising the process of producing a lithium initiator and subsequently in using the said initiator to produce polymers containing the said protecting groups as compared to using substituted silyl protecting groups are as follows: 1) cheaper and more readily available raw materials are used in the preparation of initiators, e.g.inexpensive olefins such as isobutylene or isoamylene are reacted with omega halo-alcohol as compared to the use of the more expensive alkyl chlorosilanes, such as tert-butyldimethylchlorosilane or diphenylmethylchlorosilane. 2) The excellent stability of the protective group to most reagents except strong acids [comparable to tert-butyldimethylsilyl group] 3) The protecting groups of this invention can be removed in as many ways and as simply as any of the substituted silyl protecting groups. Thus, for example, a tert-butyl protecting group on a hydroxy terminated polymer can be removed with a) anhydrous triflic acid b) HBr in acetic acid c) HCl in dioxane d) acetic anhydride in ethyl ether (FeCl3 catalyst) e) TiCl4 in CH2Cl2 ( T. W. Greene, Protective Groups in Organic Chemistry, Wiley, New York, 1981, pp 41–42 ) f) catalytic amounts of tert-butyldimethylsilyl triflate in methylene chloride ( X. Frank et al, Tetrahedron Letters, 36, (5), 711 (1995). g) Amberlyst acidic ion exchange resin may also be employed at elevated temperatures. 4) The by-products of the deprotection step are easy to remove from the polymer. For example, the by-product of the deprotection reaction of the tert-butyl protected hydroxypolymer is isobutylene, which is innocuous and does not require removal from the polymer, although it can be removed easily at temperatures above 100 degrees C. during deprotection (see U.S. Pat. No. 4,886,446). The by-product of the deprotection of an alkylsilyl protected hydroxy polymer is an alkylsiloxane which is a contaminant that may require removal from the polymer.

Anionic polymerizations employing the herein described monofunctional ether initiators of this invention are conducted in an inert solvent, preferably a non-polar solvent, optionally containing an ethereal modifier, using an olefinic monomer which is an alkene or a 1,3-diene at a temperature of about −30° C. to about +100° C. The polymerization reaction proceeds from initiation to propagation and finally termination so that the polymer is mono-functional or dysfunctional terminated. The polymers have molecular weight ranges of about 1000 to 10,000. Typically 5 to 50 millimoles of initiator is used per mole of monomer.

The present invention also provides a process for the anionic polymerization of anionically polymerizable monomers comprising the steps of:

a) initiating polymerization of a conjugated diene hydrocarbon monomer or an alkenylsubstituted aromatic hydrocarbon monomer in a hydrocarbon or mixed hydrocarbon-polar solvent medium at a temperature of 10° C. to 70° C. with an initiator having the formula:

$$M-Z-OC(R^1R^2R^3) \quad (II)$$

wherein M is an alkali metal, preferably lithium, Z is defined as a branched or straight chain hydrocarbon connecting group which contains 3–25 carbon atoms, optionally containing aryl or substituted aryl groups; and $R^1$, $R^2$, and $R^3$ are independently selected from hydrogen, alkyl, substituted alkyl, aryl or substituted aryl groups to produce an intermediate polymer of formula Li—(Q)m—Z—OC($R^1R^2R^3$) wherein Q is a unit of polymerized conjugated diene or alkenylsubstituted aromatic hydrocarbon and Z, $R^1R^2$ and $R^3$ have the meanings ascribed above, m is the number of units to the polymerized conjugated diene or alkenylsubstiuted aromatic hydrocarbon and may vary from 10 to 200 units, reacting the intermediate polymer with a compound selected from ethyene oxide, oxygen, carbon dioxide, sulfur, omega-alkenylarylhalosilanes (as exemplified by styrenyldimethylchlorosilane), isomeric divinylbenzenes, chlorosilanes (as exemplified by silicon tetrachloride and dimethyldichlorosilane, and chlorostannanes (as exemplified by tin tetrachloride and dibutyltin dichloride) and other materials known in the art to be useful for terminating, end capping or coupling of polymers; optionally hydrogenating the polymer; and b) recovering a linear or branched polymer having one or more terminal functional groups, having the formula FG—(Q)m—Z—OC(R1R2R3) wherein FG is a functional group derived by reaction of the intermediate polymer with one of the selected functionalizing compounds described above and m is the number of units of the polymerized cojugated diene or alkenylsubstituted aromatic hydrocarbon and may vary from 10 to 200, c) further reacting the functional polymer with other comonomers such as diesters, diisocyanates, di- or cyclic amides, and diols in the presence of a strong acid catalyst to simultaneously deprotect the fuctional polymer and polymerize both functional ends thereof to produce novel segmented block polymers, or d) further reacting the functional polymer with other comonomers in the absence of a strong acid catalyst to yield novel block polymers, while maintaining the integrity of the protective group, or e) further removing the protective group from the resultant polymer from d) above followed by reaction with the same or other comonomers to produce novel segmented block polymers.

The olefinic monomer to be anionically polymerized by the monofunctional ether initiator is a conjugated polyene hydrocarbon having from 4 to 30 carbon atoms, preferably a conjugated diene, or an alkenylaromatic hydrocarbon. The conjugated diene or alkenylaromatic compound will be chosen from the group of unsaturated organic compounds that can be polymerized anionically (i.e., in a reaction initiated by an organo-alkali metal). Suitable alkenylaromatics include the optionally-substituted styrenes and vinylnaphthalenes. Alkenylsubstituted aromatic hydrocarbons useful in practicing this invention include but are not limited to styrene, alphamethylstyrene, vinyltoluene, 1-vinylnapthalene, 3-methylstyrene, 4-methylstyrene, 1,1-diphenylethylene and the like. Suitable 1,3-dienes will preferably contain from 4 to 12, especially from 4 to 8, carbon atoms per molecule. Examples of these compounds include, but are not limited to, the following: 1,3-butadiene, isoprene; 2,3-dimethyl-1,3-butadiene, 1,3-pentadiene, 2-methyl-3-ethyl-1,3-butadiene, 2-methyl-3-ethyl-1,3-pentadiene, 1,3-hexadiene, 2-methyl-1,3-hexadiene, 2,5-dimethyl-1,3-hexadiene, 1,3-heptadiene, 3-methyl-1,3-heptadiene, 1,3-octadiene, 3-butyl-1,3-octadiene, 3,4-dimethyl-1,3-hexadiene; 3-n-propyl-1,3-pentadiene, 4,5-diethyl-1,3-octadiene, 2,4-diethyl- 1,3-butadiene, 2,3-di-n-propyl-1,3-butadiene, and 2-methyl-3-isopropyl-1,3-butadiene.

Among the dialkylbutadienes, it is preferred that the alkyl groups contain from 1 to 3 carbon atoms. Of the above monomers 1,3-butadiene, isoprene, 2,3-dimethyl-1,3-butadiene and 1,3-pentadiene are preferred with 1,3-butadiene being particularly preferred. The dienes may be polymerised alone, or in admixture with each other or with alkenylaromatic compounds to form random copolymers, or by charging the dienes to the reaction mixture sequentially, either with each other or with alkenylaromatic compounds, to form block copolymers.

For example, a protected functional living polymer of this invention can be generated by polymerizing 1,3-butadiene with an initiator of formula I above, wherein M is lithium, Z is a trimethylene or connecting group, and $R^1$, R, and $R^3$ are methyl groups. A living polymer is produced having the formula $$Li-(B)m-(CH_2)_3-O-C(CH_3)_3 \quad (III)$$

where B is a unit derived by polymerizing butadiene, and m is an integer from about 10 to 200. The living polymer III, may be reacted, for example, with ethylene oxide to yield, after hydrolysis, the compound of formula $$HOCH_2CH_2—(B)_m—(CH_2)_3—O—C(CH_3)_3 \quad (IV)$$

which may optionally be hydrogenated to the corresponding asymmetric polymer.

Additionally, other asymmetrically difunctional polymers may be produced by reacting the living polymer (III) above with, for example, carbon dioxide to produce, a polymer with one protected hydroxyl and one carboxyl group, or the living polymer III may be reacted with 1,5 diazabicyclo-(3.1.0) hexane as described in U.S. Pat. No. 4,753,991 to produce a polymer with one protected hydroxyl and one amino group.

Other asymmetrically substituted monofunctional polymers may be produced having epoxy or isocyanate groups at one end for example by reacting the lithium salt of IV above (before hydrolysis), with epichlorohydrin or, by reacting IV itself with an equivalent of a diisocyanate, such as methylene 4,4-diphenyl diisocyante (2/1 NCO/OH). These unsymmetrically substituted difunctional polymers could then be further reacted with other comonomers either with or without simultaneous deprotection as described above.

The protected monohydroxy polymers (IV) alone and in their hydrogenated forms, could be used as base materials to lend flexibility and higher impact strength in a number of formulas to produce coatings, sealants, binders and block copolymers with polyesters, polyamides and polycarbonates as described in UK Patent Application GB2270317A and in "Polytail" data sheets and brochures (Mitsubishi Kasei America).

Thus, in the presence of acidic catalysts used to promote the formation of many of these block copolymer resins, the protective group of the hydrogenated polymer is removed as well, allowing the exposed hydroxyl grouping in the base polymer molecule to simultaneously participate in the block copolymer reaction.

Thus, for example, hydrogenated IV polymers may be reacted with bisphenol A and phosgene in the presence of appropriate catalysts with simultaneous deprotection to yield a polycarbonate alternating block copolymer. The resulting products are useful as molding resins, for example, to prepare interior components for automobiles.

A segmented polyamide-hydrogenated IV block copolymer also useful as a molding composition to prepare exterior automotive components can be prepared by reacting hydrogenated IV polymer with caprolactam and adipic acid in the presence of a suitable catalyst.

A segmented polyester-hydrogenated IV block copolymer can be produced by reaction of hydrogenated IV polymer with dimethyl terephthalate and a suitable acidic catalyst. Again, the products are useful as molding compounds for exterior automotive components.

Isocyanate-terminated prepolymers can be produced from hydrogenated IV polymers by reaction with suitable diisocyanates (2/1 NCO/OH) as above which can be further reacted with diols and additional diisocyanates to form segmented polyurethanes useful for water based, low VOC coatings. Or segmented polyurethane prepolymers may be mixed with tackifying resins and used as a moisture-curable sealant, caulk or coating.

An acrylate-terminated prepolymer curable by free-radical processes can be prepared from the hydrogenated IV polymer by reaction with a diisocyanate (2NCO/OH) followed by further reaction with hydroxyethyl acrylate in the presence of a basic reagent.

Alternatively, the protected monohydroxy terminated polymer (IV) may be reacted with functional comonomers, wihout simultaneously removing the protective group, to produce novel copolymers. These copolymers may be deprotected and then furthur reacted with the same or different comonomers to form yet other novel copolymers. Thus, for example, the hydroxyterminated polymer of formula (IV) may be hydrogenated, and then reacted with ethylene oxide in the presence of potassium tert-butoxide to produce a poly(ethleneoxide)-hydrogenated polybutadiene copolymer with one protected hydroxyl group on the polybutadiene segment. This hydroxyl can then be deprotected and a poly(ethyleneoxide) polymer having different chain lengths grown onto both ends of the polybutadiene segment.

These processes can be applied to the deprotected and optionally hydrogenated polymers of formula IV, as well. Thus, alternatively, the protective group could be removed first from the hydrogenated polymer, and then the block copolymers formed by addition of the appropriate comonomers.

In another possible application, the living polymer III may be reacted with an alkenylarylhalosilane such as styrenyldimethylchlorosilane to yield the corresponding omega-styrenylterminated macromonomer according to directions in U.S. Pat. No. 5,278,244 which may be further polymerized by a variety of techniques to yield "comb" polymers which, on deprotection and hydrogenation yield branched polymers with hydroxyfunctionality on the branch-ends. Such multi-functionality can be utilized to graft a water-soluble polymer such as polyethylene oxide onto a hydrophobic polyolefinic core to produce hydrogels.

In still another example, a living polymer analogous to III having the formula $$Li(B)x(S)y(CH2)3—OC(CH3)3$$

where B is polymerized butadiene, S is polymerized styrene and x and y can vary from 10 to 1000 or more is reacted with divinylbenzene (DVB) to produce a multi-armed star polymer, according to U.S. Pat. No. 4,409,357 which on hydrogenation and deprotection would yield a star with hydroxyfunctional branches which may be furthur reacted with ethylene oxide and potassium alkoxide as described above to produce hydrogels.

In still another possible application, the hydrogenated hydroxyterminated branches of the star polymer may be furthur reacted with acryloyl chloride or methacryloyl chloride, and the resultant acrylate or methacrylate-terminated polymer furthur polymerized with monomers selected from the group of alkyl acrylates, alkyl methacrylates, and dialkylacrylamides to produce hydrogels. Star polymers are useful as viscosity index improver for motor oils.

Other monomers may be reacted directly with formula III type compounds to yield block or star copolymers.

The following examples further illustrate the invention.

EXAMPLE 1

Preparation of 3-(1,1-Dimethylethoxy)-1-Propyllithium in Cyclohexane, Lot 8888

A 500 ml., three-necked, Morton flask was fitted with a mechanical stirrer, a 125 ml pressure-equalizing addition funnel, and a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion, lot 8200, 0.61% sodium, was washed free of mineral oil with hexane (2×70 ml), and pentane (1×70 ml). The resultant lithium dispersion was dried in a stream of argon, weighed (4.07 grams, 0.586 mole, 2.80 equivalents), and transferred to the reaction flask with 150 ml of cyclohexane. The reaction mixture was stirred at 450 RPMs, and heated to 70° C. with a heating mantle. The heat source was removed. 1-Chloro-3-(1,1-dimethylethoxy)-propane, 31.52 grams, (0.209 mole, 1.00 equivalent, lot 8864) was added dropwise via the addition funnel. An exotherm was detected after 5.5% of the halide feed had been added. A dry ice/hexane cooling bath was applied as needed to maintain the reaction temperature between 60°–65° C. The total halide feed time was fifty-two minutes. The cooling bath was removed at the end of the halide feed. The reaction temperature fell off rapidly to room temperature. The reaction mixture was stirred for one hour at 450 RPMs, and two and one half hours at 300 RPMs. The reaction mixture was transferred with argon pressure to a dry sintered glass pressure filter. The product solution was pressure filtered with 3 psi (20.68×10$^3$ Pa) argon. The lithium chloride muds were reslurried with fresh cyclohexane (2×50 ml.). The filtrate was a clear, yellow solution, yield =230 ml., 185.03 grams.

Total Base=3.85 wt. %. Active C-Li=3.78 wt. %. Yield= 27.4% (based on active analysis).

A one ml. aliquot of this solution was carefully quenched with water. The organic phase was analyzed by Gas Chromatography (30 m.×0.54 mm AT-1 column). 1-Chloro-3-(1,1-dimethylethoxy)-propane (retention time=13.58 minutes) was not detected. The corresponding des-chloro material (retention time=8.36 minutes) was identified by GC/MS.

The very thick lithium chloride mud cake was washed with dry dibutylether (3×50 ml.). This afforded a clear, colorless solution, yield=200 ml., 154.76 grams.

Total Base= 5.69 wt %. Active C-Li= 3.32 wt. %. Yield= 20.1% (based on active analysis).

The total yield was 47.6%.

EXAMPLE 2

Preparation of
3-(1,1-Dimethylethoxy)-2,2-Dimethyl-1-Propyllithium in Cyclohexane, Lot 8923

A 500 ml., three-necked, Morton flask was fitted with a mechanical stirrer, a 125 ml pressure-equalizing addition funnel, and a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion, lot 8200, 0.61% sodium, was washed free of mineral oil with hexane (2×70 ml), and pentane (1×70 ml). The resultant lithium dispersion was dried in a stream of argon, weighed (4.40 grams, 0.634 mole, 2.80 equivalents), and transferred to the reaction flask with 200 ml of cyclohexane. The reaction mixture was stirred at 450 RPMs, and heated to 65° C. with a heating mantle. The heat source was removed. 1-Chloro-3-(1,1-dimethylethoxy)-2,2-dimethyl-propane, 40.42 grams, (0.226 mole, 1.00 equivalent, lot 8913) was added dropwise via the addition funnel. An exotherm was detected after 12.8% of the halide feed had been added. A dry ice/hexane cooling bath was applied as needed to maintain the reaction temperature between 60°–65° C. The total halide feed time was one hour. The cooling bath was removed at the end of the halide feed. The reaction temperature fell off rapidly to room temperature. The reaction mixture was stirred for eighty minutes at 450 RPMs. The reaction mixture was then transferred with argon pressure to a dry sintered glass pressure filter. The product solution was pressure filtered with 3 psi (20.68×10$^3$ Pa) argon. The lithium chloride muds were reslurried with fresh cyclohexane (2×40 ml.). The filtrate was a clear, pale yellow solution, yield=320 ml., 251.91 grams. A white solid precipitated from solution immediately after the filtration.

Analysis of the supernatant solution: Total Base=7.4 wt. %. Active C-Li=7.0 wt. %. Yield=52.0% (based on active analysis). Analysis of the slurry: Total Base= 12.4 wt. %. Active C-Li= 11.9 wt. %. Yield= 88.4% (based on active analysis).

EXAMPLE 3

Preparation of
3-(1,1-Dimethylpropyloxy)-1-Propyllithium in Cyclohexane, Lot 9135

A one liter, three-necked, Morton flask was fitted with a mechanical stirrer, a 125 ml pressure-equalizing addition funnel, and a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion, lot 8899, 0.43% sodium, was washed free of mineral oil with hexane (2×100 ml), and pentane (1×100 ml). The resultant lithium dispersion was dried in a stream of argon, weighed (6.35 grams, 0.915 mole, 3.67 equivalents), and transferred to the reaction flask with 180 ml of cyclohexane. The reaction mixture was stirred at 450 RPMs, and heated to 65° C. with a heating mantle. The heat source was removed. 1-Chloro-3-(1,1-dimethylpropyloxy)-propane, 41.00 grams, (0.249 mole, 1.00 equivalent, lot 9118, 9134) was added dropwise via the addition funnel. An exotherm was detected after 13% of the feed had been added. A dry ice/hexane cooling bath was applied as needed to maintain the reaction temperature between 60°–65° C. The total halide feed time was sixty-five minutes. The cooling bath was removed at the end of the halide feed. The reaction temperature fell off gradually to room temperature. The reaction mixture was stirred for one hour at 450 RPMs, and one hour at 300 RPMs. The reaction mixture was transferred with argon pressure to a dry sintered glass pressure filter. The product solution was pressure filtered with 3 psi (20.68×10$^3$ Pa) argon. The lithium chloride muds were reslurried with fresh cyclohexane (2×50 ml.). The filtrate was a clear, pale yellow solution, yield=250 ml., 190.86 grams.

Total Base=6.32 wt. %. Active C-Li=5.01 wt. %. Yield= 28.2% (based on active analysis).

EXAMPLE 4

Preparation of
3-(1,1-Dimethylpropyloxy)-2,2-Dimethyl-1-Propyllithium in Cyclohexane, Lot 9167

A one liter, three-necked, Morton flask was fitted with a mechanical stirrer, a 125 ml pressure-equalizing addition funnel, and a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion, lot 8899, 0.43% sodium, was washed free of mineral oil with hexane (2×100 ml), and pentane (1×100 ml). The resultant lithium dispersion was dried in a stream of argon, weighed (3.33 grams, 0.480 mole, 2.86 equivalents), and transferred to the reaction flask with 150 ml of cyclohexane. The reaction mixture was stirred at 450 RPMs, and heated to 65° C. with a heating mantle. The heat source was removed. 1-Chloro-3-(1,1-dimethylpropyloxy)-2,2 -dimethyl-propane, 33.00 grams, (0.168 mole, 1.00 equivalent, lot 9152) was added dropwise via the addition funnel. An exotherm was detected after 22% of the halide feed had been added. A dry ice/hexane cooling bath was applied as needed to maintain the reaction temperature between 60°–65° C. The total halide feed time was fifty-three minutes. The cooling bath was removed at the end of the halide feed. The reaction temperature fell off gradually to room temperature. The reaction mixture was stirred for forty-five minutes at 450 RPMs, and seventy-five minutes at 300 RPMs. The reaction mixture was transferred with argon pressure to a dry sintered glass pressure filter. The product solution was pressure filtered with 3 psi (20.68×10$^3$ Pa) argon. The lithium chloride muds were reslurried with fresh cyclohexane (2×50 ml.). The filtrate was a clear, pale yellow solution, yield=250 ml., 194.93 grams.

Total Base=12.4 wt. %. Active C-Li=11.3 wt. %. Yield= 78.3% (based on active analysis).

EXAMPLE 5

Preparation of 4-Methoxy-1-Butyllithium in Cyclohexane Lot 8916

A 500 ml., three-necked, Morton flask was fitted with a mechanical stirrer, a 125 ml pressure-equalizing addition funnel, and a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion, lot 8200, 0.61% sodium, was washed free of mineral oil with hexane (2×70 ml), and pentane (1×70 ml). The resultant lithium dispersion was dried in a stream of argon, weighed (7.25 grams, 1.045 mole, 2.80 equivalents), and transferred to the reaction flask with 200 ml of cyclohexane. The reaction mixture was stirred at 450 RPMs, and heated to 72.6° C. with a heating mantle. The heat source was removed. 1-Chloro-4-methoxy-butane, 45.70 grams, (0.373 mole, 1.00 equivalent, lot 8663) was added dropwise via the addition funnel. An exotherm was detected after 7.8% of the feed had been added. Hexane/dry ice cooling was applied to maintain the reaction temperature at 60°–65° C. The total halide feed time was sixty-five minutes. The cooling bath was removed at the end of the halide feed. The reaction temperature fell off rapidly to room temperature. The reaction mixture was stirred for one hour at 450 RPMs. The reaction mixture was then transferred with argon pressure to a dry sintered glass pressure filter. The product solution was pressure filtered with 3 psi (20.68×10$^3$ Pa) argon. The lithium chloride muds were reslurried with fresh cyclohexane (2×40 ml.). The filtrate was a clear, very pale yellow solution, yield=300 ml., 242.28 grams.

Total Base=12.4 wt. %. Active C-Li=12.1 wt. %. Yield= 83.6% (based on active analysis).

EXAMPLE 6

Preparation of 3-Methoxy-1-Butyllithium in Cyclohexane, Lot 8939

A 500 ml., three-necked, Morton flask was fitted with a mechanical stirrer, a 125 ml pressure-equalizing addition funnel, and a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion, lot 8899, 0.43% sodium, was washed free of mineral oil with hexane (2×70 ml), and pentane (1×70 ml). The resultant lithium dispersion was dried in a stream of argon, weighed (6.35 grams, 0.915 mole, 2.80 equivalents), and transferred to the reaction flask with 200 ml of cyclohexane. The reaction mixture was stirred at 450 RPMs, and heated to 68° C. with a heating mantle. The heat source was removed. 1-Chloro-3-methoxy-butane, 40.03 grams, (0.327 mole, 1.00 equivalent, lot 8914) was added dropwise via the addition funnel. An exotherm was detected after 7.5% of the feed had been added. A dry ice/hexane cooling bath was applied as needed to maintain the reaction temperature between 60°–65° C. The total halide feed time was eighty-three minutes. The cooling bath was removed at the end of the halide feed. The reaction temperature fell off rapidly to room temperature. The reaction mixture was stirred for one hour at 450 RPMs. The reaction mixture was then transferred with argon pressure to a dry sintered glass pressure filter. The product solution was pressure filtered with 3 psi (20.68×10$^3$ Pa) argon. The lithium chloride muds were reslurried with fresh cyclohexane (2×75 ml.). The filtrate was a clear, pale yellow solution, yield=280 ml., 215.70 grams.

Total Base=13.58 wt. %. Active C-Li=13.12 wt. %. Yield=92.1% (based on active analysis). Soluble chloride= 62 ppm.

EXAMPLE 7

Preparation of 4-(2-Butoxy)-1-Butyllithium in Cyclohexane, Lot 8956

A 500 ml., three-necked, Morton flask was fitted with a mechanical stirrer, a 125 ml pressure-equalizing addition funnel, and a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion, lot 8899, 0.43% sodium, was washed free of mineral oil with hexane (2×100 ml), and pentane (1×100 ml). The resultant lithium dispersion was dried in a stream of argon, weighed (6.70 grams, 0.965 mole, 2.80 equivalents), and transferred to the reaction flask with 250 ml of cyclohexane. The reaction mixture was stirred at 450 RPMs, and heated to 65° C. with a heating mantle. The heat source was removed. 4-(2-Butoxy)-1 -chloro-butane, 56.72 grams, (0.345 mole, 1.00 equivalent, lot 8921) was added dropwise via the addition funnel. An exotherm was detected after 15.6% of the halide feed had been added. A dry ice/hexane cooling bath was applied as needed to maintain the reaction temperature between 60°–65° C. The total halide feed time was seventy-two minutes. The cooling bath was removed at the end of the halide feed. The reaction temperature fell off rapidly to room temperature. The reaction mixture was stirred for one hour at 450 RPMs. The reaction mixture was then transferred with argon pressure to a dry sintered glass pressure filter. The product solution was pressure filtered with 3 psi (20.68×10$^3$ Pa) argon. The lithium chloride muds were reslurried with fresh cyclohexane (1×75 ml., 1×50 ml.). The filtrate was a clear, yellow solution, yield=440 ml., 348.84 grams.

Total Base=12.1 wt. %. Active C-Li=11.2 wt. %. Yield= 83.3% (based on active analysis).

EXAMPLE 8

Preparation of 4-(1-Methylethoxy)-1-Butyllithium in Cyclohexane, Lot 9042

A 500 ml., three-necked, Morton flask was fitted with a mechanical stirrer, a 125 ml pressure-equalizing addition funnel, and a Claisen adapter equipped with a thermocouple, a dry ice condenser, and an argon inlet. This apparatus was dried in an oven overnight at 125° C., assembled hot, and allowed to cool to room temperature in a stream of argon. Lithium metal dispersion, lot 8899, 0.43% sodium, was washed free of mineral oil with hexane (2×70 ml), and pentane (1×70 ml). The resultant lithium dispersion was dried in a stream of argon, weighed (6.00 grams, 0.864 mole, 2.80 equivalents), and transferred to the reaction flask with 250 ml of cyclohexane. The reaction mixture was stirred at 450 RPMs, and heated to 80° C. with a heating mantle. The heat source was removed. 1-Chloro-4-(1-methyoxy)-butane, 46.47 grams, (0.309 mole, 1.00 equivalent, lot 8960) was added dropwise via the addition funnel. An exotherm was detected after 22.9% of the halide feed had been added. A dry ice/hexane cooling bath was applied as needed to maintain the reaction temperature between 60°–65° C. The total halide feed time was forty-five minutes. The cooling bath was removed at the end of the halide feed. The reaction temperature fell off rapidly to room temperature. The reaction mixture was stirred for ninety minutes at 450 RPMs, then for two hours at 300 RPMs. The reaction mixture was then transferred with argon pressure to a dry sintered glass pressure filter. The product solution was pressure filtered with 3 psi (20.68×10$^3$ Pa) argon. The lithium chloride muds were reslurried with fresh cyclohexane (2×25 ml.). The filtrate was a clear, yellow solution, yield=350 ml., 264.91 grams.

Total Base=12.3 wt. %. Active C-Li=11.0 wt. %. Yield=77.3% (based on active analysis).

POLYMERIZATION EXAMPLE

Polymerization of Isoprene with 4-Methoxy-1-Butyllithium, Lot 8970

A one liter, three-necked, round-bottom flask was fitted with a mechanical stirrer, a septum and a Claisen adapter equipped with a thermocouple, dry ice condenser, and an argon inlet. This apparatus was dried in an oven overnight at 125° C., assembled hot, and allowed to cool to room temperature in a stream of argon. The flask was charged with cyclohexane, 310.70 grams, and isoprene, 40.00 grams (0.587 mole). The reaction mixture was at 20.0° C. 4-Methoxy-1-butyllithium, 16.74 grams of 11.4 wt. % solution (0.020 mole, Lot 8915) was then added with a syringe. An exotherm of 1° C. was detected. The clear solution was heated to 48.4° C. with a heating mantle. The heat source was removed. The reaction temperature proceeded to climb steadily to 53.4° C., at which time a dry ice/hexane cooling bath was employed for a few minutes to moderate the temperature. The cooling bath was then removed. The reaction temperature gradually declined to 24.2° C. in one hour. The reaction mixture was stirred at room temperature for sixteen hours, then quenched with methanol (40 ml.) and hexane (100 ml.). The reaction mixture was transferred to a one liter separatory funnel, and the methanol layer was discarded. The hydrocarbon layer was washed with an additional 40 ml. of methanol, and concentrated to constant weight on the rotary evaporator, at a bath temperature of 35° C. This afforded a clear, somewhat viscous oil, yield=39.00 grams (97.3%).

VPO analysis, Mn=1996. GPC analysis, MWD=1.48.

The remaining polymerization data is collected in the Table.

PREPARATION OF STARTING MATERIALS

1. 1-Chloro-3-(1,1-Dimethylethoxy)-Propane, Lot 8864

A two liter, three-necked round bottom flask was fitted with a mechanical stirrer, a gas inlet tube, and a Claisen adapter equipped with a dry ice condenser, and a thermocouple. This apparatus was dried in an oven overnight at 125° C., assembled hot, and allowed to cool to room temperature in a stream of argon. The flask was charged with 141.81 grams (1.50 moles, 1.00 equivalent) of 3-chloro-1-propanol and 500 ml. of cyclohexane. The resultant two-phase solution was stirred at 400 RPMs. Amberlyst 15 resin catalyst, 35 grams, was added, followed by an additional 250 ml. of cyclohexane. A total of 93 grams (1.657 moles, 1.105 equivalents) of 2-methylpropene was discharged from the cylinder in two and a third hours. A modest exotherm was noted during the addition. The reaction mixture was stirred at 20°–25° C., and periodically monitored by gas chromatography (GC) for the disappearance of 3-chloro-1-propanol. After stirring at room temperature for twenty-eight hours, the conversion to the desired product was 94.7%. The catalyst was removed by filtration through a piece of fluted filter paper. The reaction flask was rinsed with fresh cyclohexane (2×100 ml.). The product was purified by distillation from 10.72 grams of potassium carbonate through a twelve inch Vigreux column, at atmospheric pressure. This afforded a clear, colorless oil, yield=158.42 grams (70.2%).

B.P.=151.0°–154.8° C. GC assay=0.59% 2-methylpropene, 2.54% cyclohexane, 87.15% desired product, and 9.72% unknowns. NMR (CDCl$_3$): 3.63 (t, J=6 Hz, 2H), 3.46 (t, J=6 Hz, 2H), 2.28–1.62 (m, 2H), 1.21 (s, 9H) ppm.

2. 1-Chloro-3-(1,1-Dimethylethoxy)-2,2-Dimethyl-Propane Lot 8913

A one liter, three-necked round bottom flask was fitted with a mechanical stirrer, a gas inlet tube, and a Claisen adapter equipped with a dry ice condenser, and a thermocouple. This apparatus was dried in an oven overnight at 125° C., assembled hot, and allowed to cool to room temperature in a stream of argon. The flask was charged with 91.95 grams (0.75 moles, 1.00 equivalent) of 3-chloro-2,2-dimethyl-1-propanol and 200 ml. of cyclohexane. The resultant one-phase solution was stirred at 400 RPMs. Amberlyst 15 resin catalyst, 15 grams, was added, followed by an additional 50 ml. of cyclohexane. A total of 48.4 grams (0.86 moles, 1.15 equivalents) of 2-methylpropene was discharged from the cylinder in three and a half hours. A modest exotherm was noted during the addition. The reaction mixture was stirred at 20°–25° C., and periodically monitored by gas chromatography (GC) for the disappearance of 3-chloro-2,2-dimethyl-1-propanol. After stirring at room temperature for twenty hours, all the starting material had been consumed, with the formation of a single, higher-boiling compound. The catalyst was removed by filtration through a piece of fluted filter paper. The reaction flask was rinsed with fresh cyclohexane (2×50 ml.). The product was purified by distillation from 5.07 grams of potassium carbonate through a twelve inch Vigreux column, at atmospheric pressure. This afforded a clear, colorless oil, yield=111.21 grams (83.0%).

B.P.=169.0°–174.0° C. GC assay=2.98% cyclohexane, 16.79% 3-chloro-2,2-dimethyl-1-propanol, 78.06% desired product, and 1.17% unknowns.

3. 1-Chloro-3-(1,1-Dimethylpropyloxy)-Propane, Lot 9245

A 500 ml., three-necked round bottom flask was fitted with a reflux condenser, a thermocouple, a septum inlet, a magnetic stir bar, and an argon inlet. The flask was charged with 3-chloro-1-propanol, 94.54 grams (1.00 mole, 1.00 equivalents), pentane (50 ml.), and 2-methyl-2-butene, 70.44 grams (1.00 mole, 1.00 equivalents). This afforded a two phase solution. The reaction mixture was maintained at 20°–25° C. with a water cooling bath. Boron trifluoride etherate, 13.85 grams (0.098 mole, 0.098 equivalents) was added rapidly via syringe. A mild exotherm, 4°–5° C., ensued, which subsided in fifteen minutes. The reaction mixture was stirred at 20°–25° C., and periodically monitored by gas chromatography (GC) for the disappearance of 3-chloro-1-propanol. After forty-eight hours stirring, all the starting material had been consumed, and the reaction mixture was a single phase. The reaction mixture was diluted with pentane (100 ml.) and water (100 ml.) and transferred to a separatory funnel. The aqueous layer was discarded. The organic layer was washed with saturated sodium bicarbonate solution (2×50 ml.), water (1×50 ml.), and filter-dried over magnesium sulfate. The filtrate was concentrated on the rotary evaporator at room temperature to afford a pale yellow liquid, yield=113.47 grams (69.0%).

GC assay=96.7% desired product, 3.3% unknowns. NMR (CDCl$_3$): 3.65 (t, J=6 Hz, 2H), 3.45 (t, J=6 Hz, 2H), 2.00 (q, J=6 Hz, 2H), 1.80–1.25 (m, 2H), 1.13 (s, 6H), and 0.84 (t, J=6 Hz, 3H) ppm.

4. 1-Chloro-3-(1,1-Dimethylpropyloxy)-2,2-Dimethyl-Propane, Lot 9250

A 500 ml., three-necked round bottom flask was fitted with a reflux condenser, a thermocouple, a septum inlet, a magnetic stir bar, and an argon inlet. The flask was charged with 3-chloro-2,2-dimethyl-1-propanol, 122.60 grams (1.00 mole, 1.00 equivalents), pentane (50 ml.), and 2-methyl-2-butene, 70.66 grams (1.01 mole, 1.01 equivalents). This afforded a two phase solution. The reaction mixture was maintained at 20°–25° C. with a water cooling bath. Boron trifluoride etherate, 13.85 grams (0.098 mole, 0.098 equivalents) was added rapidly via syringe. A mild exotherm, 4°–5° C., ensued, which subsided in fifteen minutes. The reaction mixture was stirred at 20°–25° C., and periodically monitored by gas chromatography (GC) for the disappearance of 3-chloro-2,2-dimethyl-1-propanol. After twenty-four hours stirring, all the starting material had been consumed, and the reaction mixture was a single phase. The reaction mixture was diluted with pentane (50 ml.) and water (100 ml.) and transferred to a separatory funnel. The aqueous layer was discarded. The organic layer was washed with saturated sodium bicarbonate solution (2×50 ml.), water (1×50 ml.), and filter-dried over magnesium sulfate. The filtrate was concentrated on the rotary evaporator at room temperature to afford a clear, almost colorless liquid, yield=165.90 grams (86.1%).

GC assay=87.7% desired product, 12.3% unknowns. NMR (CDCl$_3$): 3.45 (s, 2H), 3.09 (s, 2H), 1.81–1.20 (m, 2H), 1.09 (s, 6H), 0.95 (s, 6H), and 0.84 (t, J=6 Hz, 3H).

5. 1-Chloro-4-Methoxy-Butane, Lot 8663

A one liter, three-necked round bottom flask was equipped with a reflux condenser, a teflon clad thermocouple, a 225 ml. pressure-equalizing addition funnel, a large egg-shaped magnetic stir bar, and a gas outlet vented to a caustic scrubber. This apparatus was dried in an oven overnight at 125° C., assembled hot, and allowed to cool to room temperature in a stream of argon. The flask was charged with methanol, 80.10 grams (2.50 moles, 1.00 equivalent) and tetrahydrofuran, 180.28 grams (2.50 moles, 1.00 equivalent). The reaction mixture was cooled to 0° C. with a methanol/ice bath, then 356.91 grams (3.00 moles, 1.20 equivalents) of thionyl chloride was added dropwise via the addition funnel. There was an immediate exotherm, and a release of acidic fumes. The temperature was held below 15° C. by adjustment of the feed rate. The total thionyl chloride feed time was two and a third hours. The cooling bath was removed at the end of the feed. The reaction mixture was clear and colorless. The reaction mixture was heated to reflux for three hours, at which time the temperature was 120° C., then the reaction mixture was allowed to cool to room temperature. An aliquot was withdrawn, diluted with pentane, washed with water and saturated sodium bicarbonate solution, then analyzed by gas chromatography (30 m.×0.54 mm AT-1 column). Both of the starting materials were still present, tetrahydrofuran (retention time=3.46 minutes), methanol (retention time=0.85 minutes), in addition to the desired product (retention time=8.68 minutes). The reaction mixture was heated to reflux for an additional two hours, after which time all gas evolution had ceased. The reaction mixture was allowed to cool to room temperature, then the orange reaction mixture was transferred to a one liter separatory funnel, and diluted with pentane (300 ml.). The organic layer was washed with water (2×300 ml.), saturated sodium bicarbonate solution (1×300 ml.), and finally, water (2×300 ml.). The organic layer was dried (magnesium sulfate), filtered, and purified by distillation through a six inch Vigreux column, at atmospheric pressure. This afforded a clear, colorless oil, yield=187.63 grams (59.8%).

B.P.=140.1°–146.5° C.. GC assay=0.28% methanol, 0.17% pentane, 0.64% tetrahydrofuran, 97.68% desired product, and 1.23% unknowns. NMR (D$_6$ Benzene): 3.43–2.89 (m, 4H), 3.12 (s, 3H), and 1.97–1.19 (m, 4H), ppm.

6. 1-Chloro-3-Methoxy-Butane, Lot 8914

A 500 ml., three-necked round bottom flask was equipped with a reflux condenser, a teflon clad thermocouple, a 125 ml. pressure-equalizing addition funnel, a large egg-shaped magnetic stir bar, and a gas outlet vented to a caustic scrubber. This apparatus was dried in an oven overnight at 125° C., assembled hot, and allowed to cool to room temperature in a stream of argon. The flask was charged with thionyl chloride, 124.92 grams (1.05 moles, 1.05 equivalents). 3-Methoxy-1-butanol, 104.15 grams (1.00 mole, 1.00 equivalent) was added dropwise via the addition funnel. There was an immediate exotherm, and a release of acidic fumes. The total alcohol feed time was thirty-eight minutes. The reaction mixture was dark orange at the end of the feed. The reaction mixture was heated to reflux for four hours, then let cool to room temperature. An aliquot was withdrawn, diluted with pentane, washed with water and saturated sodium bicarbonate solution, then analyzed by gas chromatography (30 m.×0.54 mm AT-1 column). All the starting material had been consumed, with the formation of a slightly faster eluting compound (3-methoxy-1-butanol retention time=10.92 minutes, product retention time=10.38 minutes). The reaction mixture was transferred to a one liter separatory funnel, diluted with pentane (300 ml.), and the organic layer was washed with water (2×300 ml.), saturated sodium bicarbonate solution (1×300 ml.), and finally, water (1×300 ml.). The organic layer was dried (magnesium sulfate), filtered, and distilled through a twelve inch Vigreux column, at atmospheric pressure. This afforded a clear, colorless oil, yield=95.39 grams (77.9%).

B.P.=124.0°–126.6° C. GC assay=1.6% pentane, 94.2% desired product, and 4.2% unknowns. NMR (CDCl$_3$): 3.99–3.43 (m, 3H), 3.35 (s, 3H), 2.13–1.59 (m, 2H), and 1.15 (t, J=6 Hz, 3H) ppm.

7. 4-(2-Butoxy)-1-Chloro-Butane, Lot 8921

A one liter, three-necked round bottom flask was equipped with a reflux condenser, a teflon clad thermocouple, a 250 ml. pressure-equalizing addition funnel, a large egg-shaped magnetic stir bar, and a gas outlet vented to a caustic scrubber. This apparatus was dried in an oven overnight at 125° C., assembled hot, and allowed to cool to room temperature in a stream of argon. The flask was charged with 2-butanol, 185.30 grams (2.50 moles, 1.00 equivalent) and tetrahydrofuran, 180.28 grams (2.50 moles, 1.00 equivalent). The reaction mixture was cooled to −15° C., then 356.91 grams (3.00 moles, 1.20 equivalents) of thionyl chloride was added dropwise via the addition funnel. There was an immediate exotherm, and a release of acidic fumes. The temperature was held below 10° C. by adjustment of the feed rate. The total thionyl chloride feed time was two and a quarter hours. The cooling bath was removed at the end of the feed. The reaction mixture was heated to reflux (95° C.) for six hours, then let cool to room temperature. An aliquot was withdrawn, diluted with pentane, washed with water and saturated sodium bicarbonate solution, then analyzed by gas chromatography (30 m.×0.54 mm AT-1 column). Both of the starting materials were still present, tetrahydrofuran (retention time=6.09 minutes), 2-butanol (retention time= 6.62 minutes), in addition to the desired product (retention time=16.78 minutes). The reaction mixture was heated to reflux for an additional four hours, after which time all gas evolution had ceased. The reaction mixture was allowed to cool to room temperature, then transferred to a one liter separatory funnel, and diluted with pentane (300 ml.). The organic layer was washed with water (2×300 ml.), saturated sodium bicarbonate solution (1×300 ml.), and finally, water (1×300 ml.). The organic layer was dried (magnesium sulfate), filtered, and purified by distillation from 3.00 grams of potassium carbonate through a twelve inch Vigreux column, at atmospheric pressure. This afforded a clear, colorless oil, yield=207.34 grams (50.4%).

B.P.=180.0°–189.6° C. GC assay=96.0% desired product, and 4.0% unknowns. NMR (CDCl$_3$): 3.72–2.91 (m, 5H), 2.03–1.12 (m, 6H), 0.99 (d, J=6 Hz, 3H), and 0.74 (t, J=6 Hz, 3H) ppm.

8. 1-Chloro-4-(1-Methylethoxy)-Butane, Lot 8960

A one liter, three-necked round bottom flask was equipped with a reflux condenser, a teflon clad thermocouple, a 250 ml. pressure-equalizing addition funnel, a large egg-shaped magnetic stir bar, and a gas outlet vented to a caustic scrubber. This apparatus was dried in an oven overnight at 125° C., assembled hot, and allowed to cool to room temperature in a stream of argon. The flask was charged with 2-propanol, 150.25 grams (2.50 moles, 1.00 equivalent) and tetrahydrofuran, 180.28 grams (2.50 moles, 1.00 equivalent). The reaction mixture was cooled to 0° C., then 356.91 grams (3.00 moles, 1.20 equivalents) of thionyl chloride was added dropwise via the addition funnel. There was an immediate exotherm, and a release of acidic fumes. The temperature was held below 15° C. by adjustment of the feed rate. The total thionyl chloride feed time was two and a half hours. The cooling bath was removed at the end of the feed. The reaction mixture was heated to reflux (119° C.) for five hours, after which time all gas evolution had ceased, then let cool to room temperature. The orange reaction mixture was transferred to a one liter separatory funnel, and diluted with pentane (300 ml.). The organic layer was washed with water (2×400 ml.), saturated sodium bicarbonate solution (1×300 ml.), and finally, water (1×300 ml.). The organic layer was dried (magnesium sulfate), filtered, and purified by distillation from 3.00 grams of potassium carbonate through a twelve inch Vigreux column, at atmospheric pressure. This afforded a clear, colorless oil, yield=234.22 grams (61.8%). B.P.=160.0°–169.0° C. G.C. assay=88.0% desired products and 12.0% unknowns.

TABLE

SYNTHESIS POLYMERS VIA FUNCTIONAL INITIATORS

| EXP. NO. | INITIATOR NO. | POLYMER | | | | | |
|---|---|---|---|---|---|---|---|
| | | MONOMER | % YIELD | Ms (Th) | Mn (VPO) | Mn (GPC) | Mw (GPC) | MWD (GPC) |
| 8970 | 8815 | ISOPRENE | 97.3 | 2472 | 1996 | 2472 | 3646 | 1.48 |
| 8993 | 8944 | ISOPRENE | 100.0 | 2034 | 2645 | 2493 | 5752 | 2.31 |
| 9244 | 9135 | ISOPRENE | 95.1 | 2107 | 2825 | 3943 | 4482 | 1.13 |
| 9267 | 9167 | ISOPRENE | 97.3 | 2200 | 2668 | 2618 | 3007 | 1.15 |

What is claimed is:

1. A process for the anionic polymerization of an anionically polymerizable monomer comprising the steps of:
   a) initiating polymerization of a conjugated polyene hydrocarbon having 4 to 30 carbon atoms or a vinyl substituted aromatic hydrocarbon in a hydrocarbon or mixed hydrocarbon-polar solvent media at a temperature of 10°–70° C. with an initiator having the formula

M—N—O—C(R$^1$R$^2$R$^3$)

wherein M is defined as an alkali metal, selected from the group consisting of lithium, sodium and potassium; Z is defined as a branched or straight chain hydrocarbon group which contains 3–25 carbon atoms, and $R^1$, $R^2$ and $R^3$ are independently selected from hydrogen, alkyl groups, and aryl groups to produce an intermediate polymer and b) reacting the intermediate polymer with a functionalizing compound to produce a functionalized polymer
  c) optionally hydrogenating the functionalized polymer
  d) further reacting the functionalized polymer with one or more comonomers in the presence of a strong acid catalyst to simultaneously deprotect the polymer and polymerize the comonomers at both functional sites or
  e) further reacting the functionalized polymer with other comonomers in the absence of strong acid catalysts, then deprotecting the resultant copolymer and
  f) further reacting the resultant copolymer with the same or other comonomers.

2. The process of claim 1 further comprising reacting the intermediate polymer with a compound selected from the group consisting of ethylene oxide, carbon dioxide, 1,5-diazabicyclo (3.1.0) hexane, N-benzylidene trimethylsilylamide, sulfur, an omega-alkenylarylhalosilane, an isomeric divinylbenzene, a chlorosilane and a chlorostannane and recovering a functionalized linear or branched polymer having one or more terminal functional groups.

3. Hydrogenation of one or more recovered polymers of claim 2 to produce a hydrogenated polymer or polymers.

4. The process of claim 1 wherein the conjugated polyene hydrocarbon is a conjugated diene selected from the group consisting of 1,3-butadiene; isoprene;2,3-dimethyl- 1,3-butadiene; 1,3-pentadiene (piperylene), 2-methyl-3-ethyl-1, 3-butadiene, 3-methyl-1,3-pentadiene, 1,3-hexadiene, 2,5-dimethyl-1,3-hexadiene and 1,3-octadiene.

5. The process of claim 1 wherein the polar solvent is selected from the group consisting of diethyl ether, triethylamine, methyl tert-butyl ether, dibutyl ether, and tributylamine.

6. The process of claim 2 further comprising reaction of the polymers of claim 2 produced from isomeric divinyl benzenes and deprotection of the resulting polymer to yield star-branched polymers with hydroxy-terminated branches.

7. The process of claim 6 wherein the star-branched polymers are hydrogenated.

8. The process of claim 7 comprising further reaction of the hydrogenated deprotected polymers of claim 7 with ethylene oxide and potassium alkoxides to produce hydrogels.

9. The process of claim 8 comprising further reaction of the hydrogenated and deprotected polymers of claim 8 with acryloyl chloride and methacryloyl chloride 10. The process of claim 9 further comprising reacting the polymers of claim 9 with alkyl acrylates, alkyl methacrylates and dialkylacrylamides to produce hydrogels.

11. The process of claim 2 wherein the functionalizing compound is ethylene oxide, the functionalized polymer is hydrogenated, and the comonomers are selected from the group of epichlorohydrin and diisocyanates to produce epoxide and isocyanate-terminated polymers.

12. The process of claim 11 further comprising simultaneous deprotection and polymerization of the isocyanate and epoxy-terminated polymers.

13. The process of claim 2 further comprising reaction of the hydrogenated polymer of claim 2 produced from ethylene oxide with comonomers selected from the group consisting of dialkylterephthalates, alpha-omega alkane diols, diisocyanates, caprolactam and adipic acid and the polymerization is carried out simultaneously with deprotection.

14. The process of claim 12 wherein the functionalizing compound is ethylene oxide, the comonomer is ethylene oxide, the polymerization is carried out in the presence of potassium tert-butoxide, the resulting copolymer is deprotected and reaction with comonomer continued.

15. The process of claim 2 wherein the functionalizing compound is ethylene oxide, the functional polymer is hydrogenated and reacted with a diisocyanate in a 2:1 ratio, further reacted with hyroxyethylacrylate in the presence of a basic catalyst, and deprotected to yield a macromonomer.

16. The process of claim 2 wherein the functionalizing compound is styrenyldimethylchlorosilane.

\* \* \* \* \*